United States Patent
Binmoeller et al.

(10) Patent No.: US 12,419,502 B2
(45) Date of Patent: Sep. 23, 2025

(54) ENDOSCOPE CONTROL METHODS

(71) Applicant: Endovision Foundation, San Francisco, CA (US)

(72) Inventors: Kenneth F. Binmoeller, San Francisco, CA (US); John P. Lunsford, San Carlos, CA (US); Hoang Phan, Milpitas, CA (US); Fiona Sander, Los Altos Hills, CA (US)

(73) Assignee: Endovision Foundation, San Francisco, CA (US)

( * ) Notice: Subject to any disclaimer, the term of this patent is extended or adjusted under 35 U.S.C. 154(b) by 0 days.

(21) Appl. No.: 18/308,624

(22) Filed: Apr. 27, 2023

(65) Prior Publication Data

US 2023/0263372 A1    Aug. 24, 2023

Related U.S. Application Data

(63) Continuation of application No. 17/768,835, filed as application No. PCT/US2020/055423 on Oct. 13, 2020, now Pat. No. 11,672,410.
(Continued)

(51) Int. Cl.
*A61B 1/00* (2006.01)
*A61B 1/018* (2006.01)

(52) U.S. Cl.
CPC .......... *A61B 1/00149* (2013.01); *A61B 1/018* (2013.01)

(58) Field of Classification Search
CPC ..... A61B 1/00149; A61B 1/018; A61B 90/57; A61B 2090/571; A61B 34/30; A61B 2034/301; A61B 1/00147; A61B 90/50
See application file for complete search history.

(56) References Cited

U.S. PATENT DOCUMENTS

| 5,380,338 A | 1/1995 | Christian |
| 5,441,042 A * | 8/1995 | Putman .................... B25J 9/042 |
| | | 600/102 |

(Continued)

FOREIGN PATENT DOCUMENTS

| CN | 205698057 U | 11/2016 |
| CN | 106461154 | 2/2017 |

(Continued)

OTHER PUBLICATIONS

International Search Report from the Patent Cooperation Treaty for PCT/US2020/055423 filed Oct. 13, 2020, dated Feb. 2, 2021, 2 pages.

(Continued)

*Primary Examiner* — Anh Tuan T Nguyen
*Assistant Examiner* — Rynae E Boler
(74) *Attorney, Agent, or Firm* — Aurora Consulting LLC; Tiffany Miller; Ashley Sloat

(57) ABSTRACT

Described herein are methods for reversibly constraining an endoscope. A method may include positioning an elongate medical device or endoscope in a holder of a clamp. A method may include actuating the holder such that one or more of a first sidewall and a second sidewall of the holder move to a clamped configuration to exert a force on the endoscope. A method may include adjusting a pad of the clamp from a first position to a second position where the pad is in contact with the endoscope in the second position.

7 Claims, 16 Drawing Sheets

Related U.S. Application Data

(60) Provisional application No. 62/914,689, filed on Oct. 14, 2019.

(56) References Cited

U.S. PATENT DOCUMENTS

| | | | |
|---|---|---|---|
| 7,857,272 B1* | 12/2010 | Hickey | A61B 90/50 248/288.31 |
| 9,067,306 B1 | 6/2015 | Lee | |
| 9,532,849 B2* | 1/2017 | Anderson | A61B 34/71 |
| 11,464,396 B2* | 10/2022 | Yahagi | A61B 1/00154 |
| 2004/0267089 A1 | 12/2004 | Otsuka et al. | |
| 2006/0235436 A1 | 10/2006 | Anderson et al. | |
| 2007/0129634 A1* | 6/2007 | Hickey | F16M 13/027 600/439 |
| 2007/0185376 A1* | 8/2007 | Wilson | A61B 90/57 600/102 |
| 2007/0265497 A1* | 11/2007 | Brown | A61B 1/24 600/101 |
| 2009/0287053 A1* | 11/2009 | Okamoto | A61B 1/00142 600/139 |
| 2018/0073528 A1 | 3/2018 | Pryor et al. | |
| 2018/0078115 A1* | 3/2018 | Gupta | A61B 1/06 |
| 2019/0117929 A1 | 4/2019 | Reinberg | |
| 2019/0175297 A1 | 6/2019 | Egle | |
| 2019/0195252 A1 | 6/2019 | Pryor et al. | |

FOREIGN PATENT DOCUMENTS

| | | |
|---|---|---|
| CN | 107708520 | 2/2018 |
| CN | 209220532 | 8/2019 |
| JP | H08224245 A | 9/1996 |
| JP | 2002224016 A | 8/2002 |
| JP | 2005036972 A | 2/2005 |
| JP | 2006061272 A | 3/2006 |
| JP | 2008017903 A | 1/2008 |
| JP | 2011226553 A | 11/2011 |
| WO | 2017169279 A1 | 10/2017 |

OTHER PUBLICATIONS

Written Opinion of the International Searching Authority for PCT/US2020/055423 filed Oct. 13, 2020, dated Feb. 2, 2021, 4 pages.
Extended European Search report dated Oct. 11, 2023 re EP 20877875.3-1126 / 4044895 PCT/US2020055423 (8 pages).
China Search Report re 2020800710818 dated Mar. 29, 2025 (5 pages).

* cited by examiner

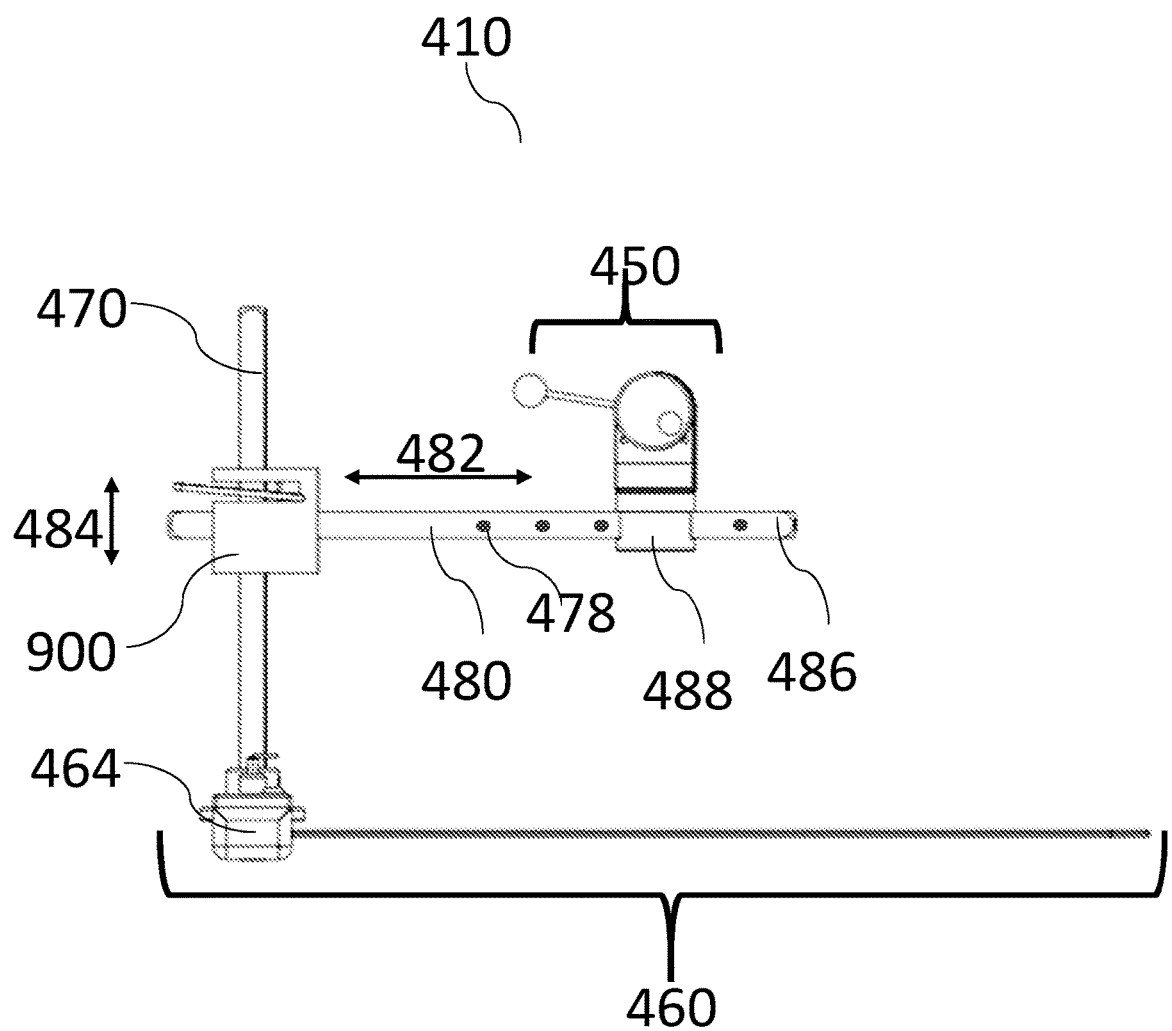
FIG. 4
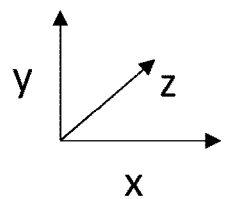

ENDOSCOPE CONTROL METHODS

CROSS-REFERENCE TO RELATED APPLICATIONS

This application is a continuation of U.S. Nonprovisional patent application Ser. No. 17/768,835, filed Apr. 13, 2022; which is a 371 U.S. National Stage Application of International PCT application PCT/US2020/055423, filed on Oct. 13, 2020; which claims the priority benefit of U.S. Provisional patent application Ser. No. 62/914,689, filed on Oct. 14, 2019, the contents of which are herein incorporated by reference.

TECHNICAL FIELD

This disclosure relates generally to the field of intraluminal devices, and more specifically to the field of endoscopy. Described herein are endoscope control devices.

BACKGROUND

Endoscopy uses thin flexible tubes that are inserted into the body's openings (e.g., mouth, anus, etc.) or through incisions to study tissues, perform biopsies, and/or deliver therapy or treatments. Frequently, organ systems such as the gastrointestinal tract, respiratory tract, urinary tract, and female reproductive tract are studied and/or treated using endoscopes. Endoscopes are also common in various types of laparoscopic procedures, where the endoscope is inserted minimally invasively into an incision near the tissue of interest. Depending on the tissue to be studied and/or the treatment to be performed, endoscopes may be equipped, either on a distal end or via passage through a lumen of the endoscope, with a diverse array of functionality: electrocauterization tools, cameras, lights, irrigation, air, ultrasound probes, resection tools (e.g., needles), etc. FIG. 1 shows an example of a typical endoscope 100. As can be seen in FIG. 1, the functionality of a typical endoscope is vast and further includes articulation knobs for articulating a distal end of the endoscope.

During endoscopy procedures, physicians must perform several tasks nearly simultaneously or in rapid succession. For example, during an endoscopy procedure, the scope needs to be stabilized, manipulated, and/or controlled translationally and rotationally without damaging the endoscope or inflicting harm on the patient. In addition, the physician needs to modulate and control air/water flow from valve 140; suction from valve 110; imaging modalities, like camera 120; treatment modalities from channel 130; etc. and articulate the distal end 150 of the endoscope 100, typically using knobs 160 for left and right articulation, as shown in FIG. 1. This immense number of tasks performed by the physician can result in physician fatigue and discomfort and ultimately damage to tendons and muscles in the physician's upper body. Further, at least one additional assistant is required to fully perform an endoscope procedure—either to hold the endoscope while various functionality of the endoscope is deployed or to operate the endoscope or a computing system in electrical communication with the endoscope, resulting in increased overhead for the hospital.

Accordingly, a device is needed for use during endoscopy procedures that performs at least a few of the tasks outlined above. Various laparoscopic assistance tools exist but are poorly equipped for the unique requirements of endoscopy. Further, devices exist that tether or adhere to the patient during the endoscope procedure. However, these devices can be uncomfortable for the patient due to the translational and rotational requirements of an endoscope during an endoscopy procedure. Robotic systems also exist for certain surgical applications but may be too cumbersome for certain endoscopy procedures. Taken together, there exists a need for new devices for endoscope control.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

FIG. 4 illustrates a side view of the endoscope control device of FIG. 2A.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

The devices described herein are configured for use with any elongate device: endoscopes, catheters, probes, etc. Exemplary non-limiting embodiments of elongate devices or endoscopes include: gastroscope, duodenoscope, colonoscope, sigmoidoscope, enteroscope, bronchoscope, ureteroscope, cystoscope, rhino-laryngoscope, laparo-thoracoscope, mobile airway scope, choledochoscope, etc.

The devices described herein may be configured for a wide variety of endoscope sizes; for example, elongate devices having an outer diameter of 9 to 11.4 mm, 10.8 to 12.5 mm, 12.9 to 13.7 mm, 21.8 to 13.2 mm, 10.5 to 11.7 mm, 5.7 to 6 mm, 2.8 to 13.2 mm, 10.5 to 11.7 mm, 5.7 to 6 mm, 2.8 to 3.3 mm, 5.4 to 5.5 mm, 2.6 to 4.9 mm, 7 mm, 4.1 to 5.2 mm, 2.8 to 5.2 mm, 5.9 to 6 mm, 11.5 to 11.6 mm, 4.4 to 5.1 mm, or any range or subrange therebetween.

Figure 1:
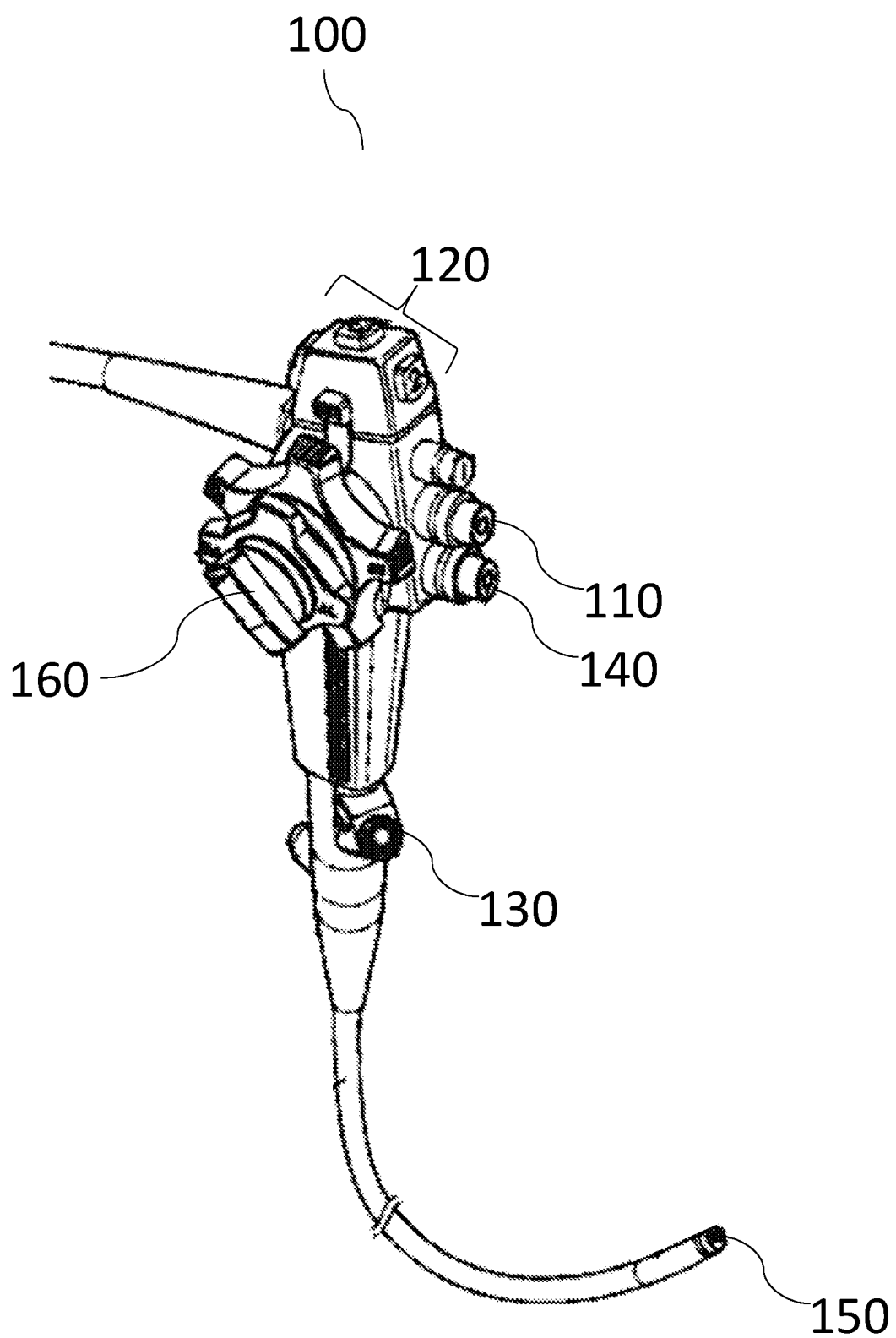
FIG. 1 illustrates a typical endoscope.
Figure 2A:
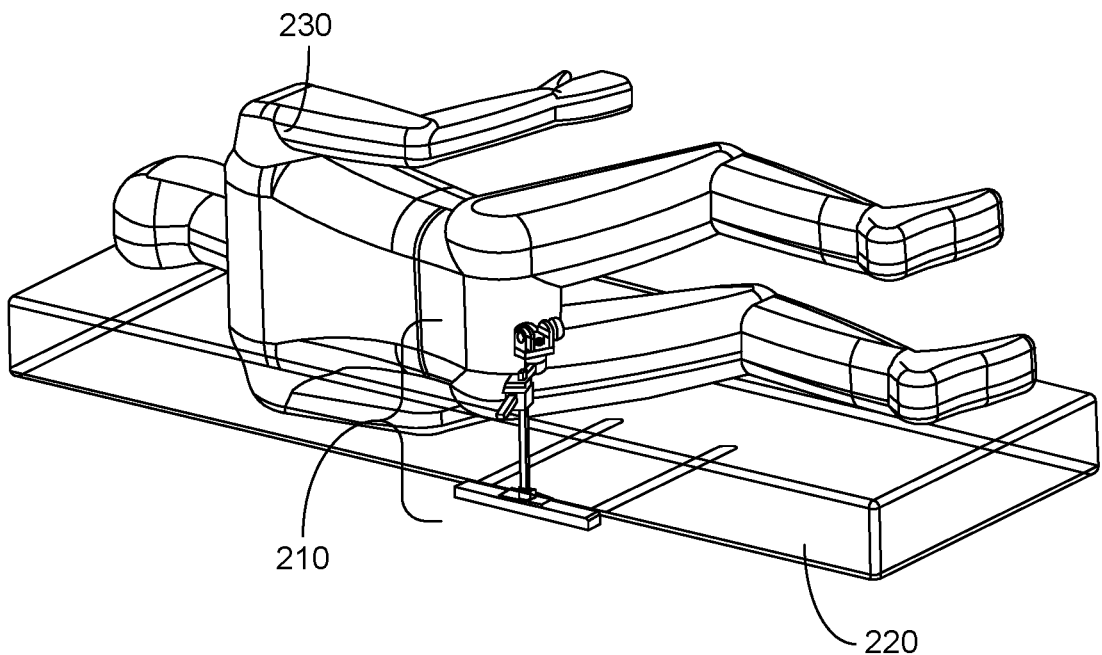
FIG. 2A illustrates one embodiment of an endoscope control device proximate to a patient.
Figure 2B:
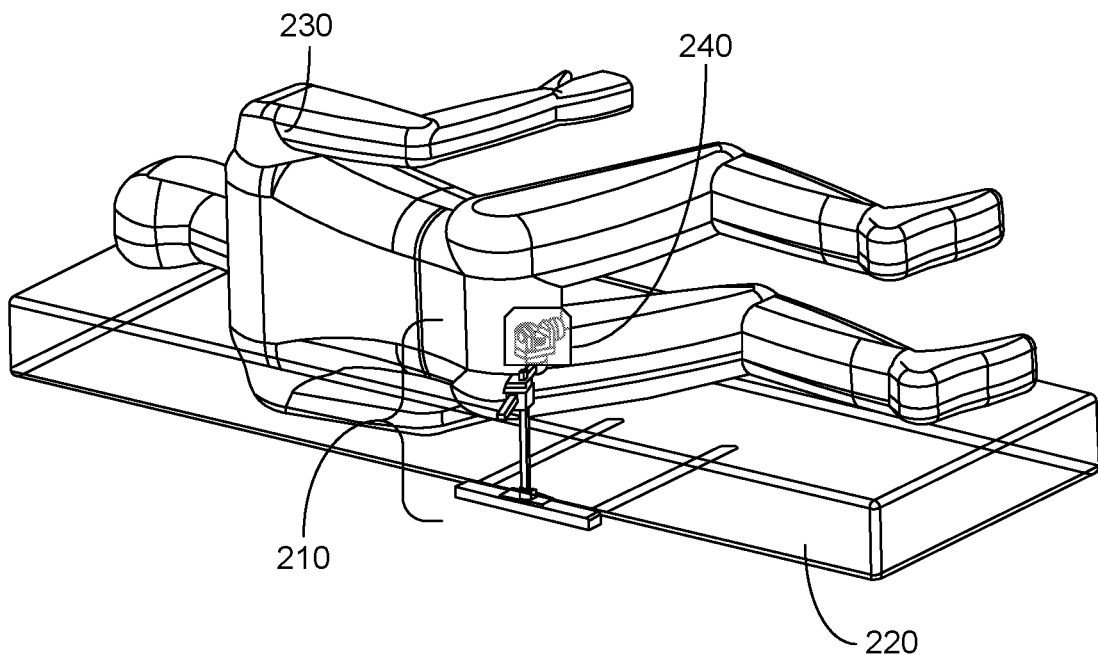
FIG. 2B illustrates one embodiment of an endoscope control device further comprising a surgical drape on at least a portion of the device.
Figure 3:
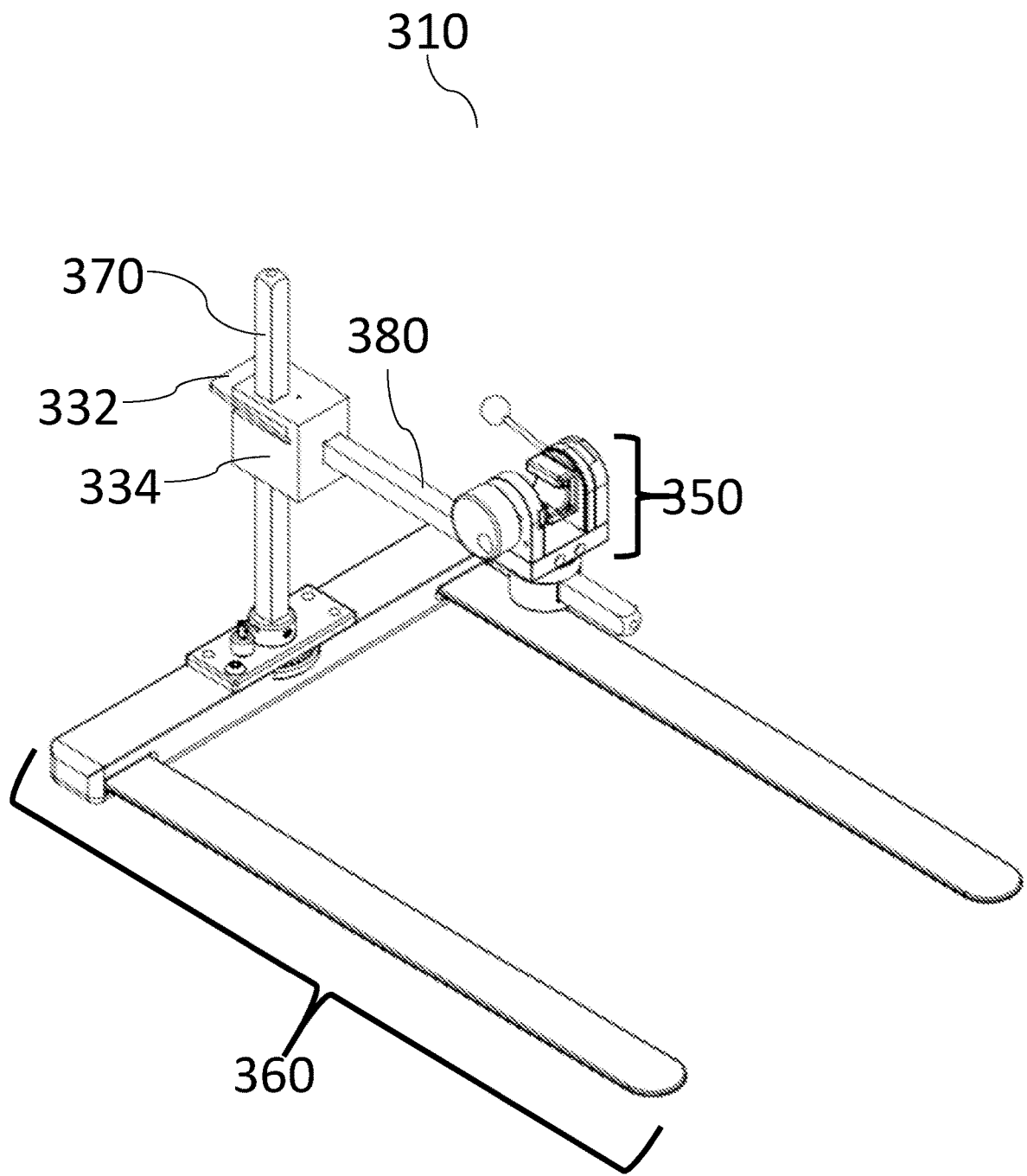
FIG. 3 illustrates a perspective view of the endoscope control device of FIG. 2A.

Disclosed herein are endoscope control devices 210. As shown in FIGS. 2A-2B, such devices, in general, include a base positionable proximate (e.g., on a bed, floor, table, stand, etc.) a patient 230, a column extending vertically from the base, an arm extending horizontally from the column, and a clamp movable or fixedly coupled to the arm. Such devices function to position an endoscope proximate to or in contact with a patient 230. A base of endoscope control device 210 may be positioned under a mattress 220 on a surgical or hospital bed or platform, such that a weight of the patient and/or mattress further stabilizes the endoscope control device 210. In other embodiments, endoscope control device 210 is positionable on the floor and comprises two or more legs (e.g., tripod, ladder configuration, etc.) or one or more wheels. For example, the endoscope control device 210 may be movable between locations on the one or more wheels. An endoscope control device 210 may be configured to be disassembled and stored and/or transported to a second location. For example, one or more legs of the base may be removable, the column may be separable from the arm and/or the base, and/or the clamp may be separable from the arm. One or more components of the endoscope control devices 210 described herein may be disposable. One or more components of the endoscope control devices 210 described herein are configured for use with a surgical drape 240, as shown in FIG. 2B, to maintain the one or more components out of the surgical field and free from contamination. The surgical drape 240 may be configured to substantially cover a clamp, arm, column, and/or base of an endoscope control device 210.

Further, the endoscope control devices 210 described herein are configured to grip an endoscope with a first, lesser force such that the endoscope remains axially and rotationally translatable; an intermediate force such that the endoscope is either axially or rotationally translatable; or with a maximum force such that the endoscope is neither axially nor rotationally translatable. Of course, there are degrees of force that restrict axial and rotational translation therebetween such that there may be an infinite number of degrees of force that impact axial and/or rotational movement of an endoscope device positioned therein. The intermediate configurations are also further configured to modulate the clamping force of a clamp from unclamped (i.e., no force applied to endoscope) to fully clamped (i.e., endoscope is completely rotationally and translationally restrained).

Figure 7:
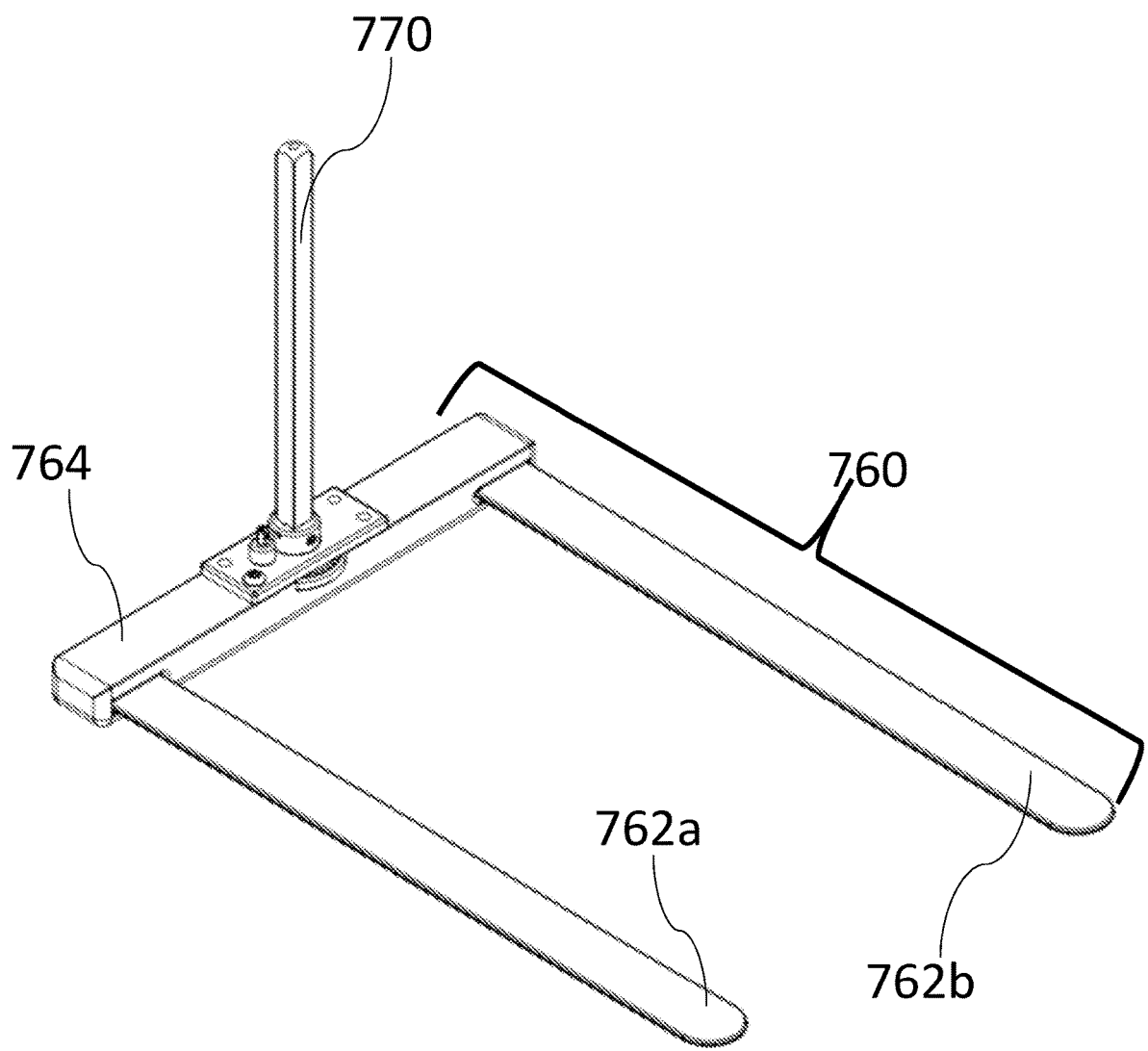
FIG. 7 illustrates a perspective view of a base and a column of an endoscope control device.
Figure 8:
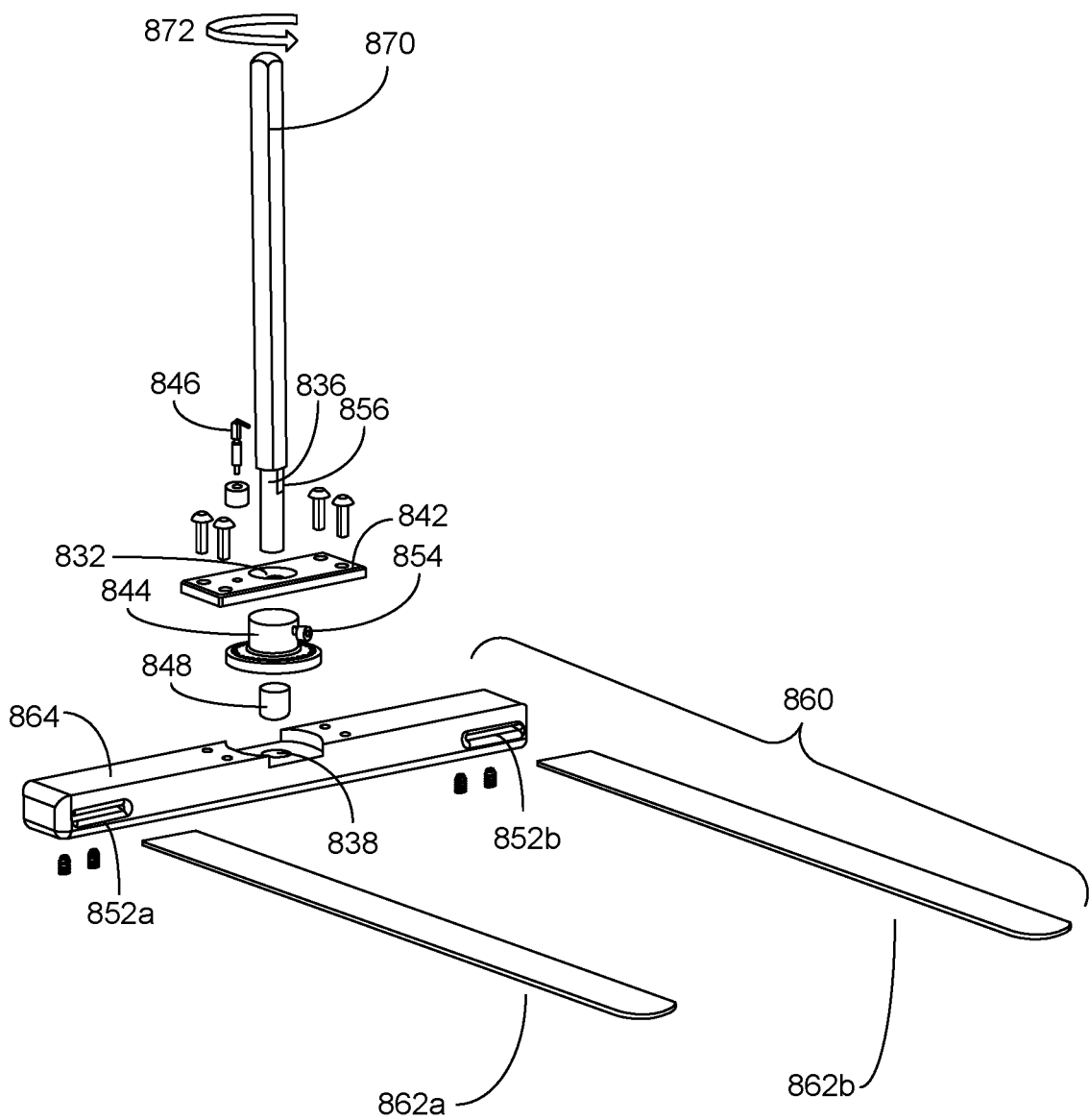
FIG. 8 illustrates an exploded view of the base and column of FIG. 7.

As shown in FIGS. 3-4 and 7-8, a device for reversibly constraining an endoscope includes a base 360, 460, 760, 860 positionable proximate a patient. The base 360, 460, 760, 860 functions to structurally support a column 370, 470, 770, 870 and an arm 380, 480 of the endoscope control device 310, 410. The base 360, 460, 760, 860 further functions to rest or be positioned on a surface, for example a floor, bed, counter, or other surface that is proximate a patient. For example, the base may be positioned such that a clamp 350, 450 of an endoscope control device 310, 410 is within 1 to 10 mm, 0.5 to 5 cm, 1 to 10 cm, or any range or subrange therebetween of a bodily opening or incision of a patient. In one non-limiting embodiment, as shown in FIGS. 7-8, base 760 (860) includes legs 762a, 762b (862a, 862b) and body 764 (864). Legs 762a, 762b (862a, 862b) are insertable under a mattress, for example, and/or rest on a surface to support the endoscope control device 310, 410. The legs 762a, 762b (862a, 862b) may comprise a lightweight material, for example aluminum, titanium, or magnesium. The legs 762a, 762b (862a, 862b) may be substantially flat, cylindrical, or otherwise. As shown in FIG. 8, legs 862a, 862b are reversibly insertable into leg receiving areas 852a, 852b defined by body 864. Legs 862a, 862b are secured via one or more fasteners (e.g., grub screws) to body 864 once positioned in leg receiving area 852a, 852b. Alternatively, legs 862a, 862b and body 864 form a monolithic support structure such that legs 862a, 862b and body 864 are irreversibly connected or machined or manufactured as one component.

As shown in FIG. 4, endoscope control device 410 further includes a column 470 extending vertically from base 460, more specifically from body 864 as shown in FIG. 8. As shown in FIG. 4, column 470 extends vertically in a y direction from a base 460 in an xz plane. Column 470 is further pivotally coupled to the base 460, more specifically body 464, such that column 470, 870 rotates around a y-axis 872, as shown in FIG. 8. Body 864 defines aperture 838 that is sized and shaped to receive connector portion 836 of column 870 through plate 842. Sleeve bearing 848 is received in aperture 838 to prevent connector portion 836 from rubbing on body 864 during rotation. Plate 842 defines aperture 832 that is configured to receive a protruding portion of rotating flange 844. Screw 854 on rotating flange 844 is configured to secure column 870 (e.g., translationally and/or rotationally) in rotating flange 844. Connector portion 836 further comprises seat 856 configured to contact screw 854 and provide torsional force on column 870. Rotating flange 844 includes a plurality of detents therein such that pin 846, when manipulated (e.g., lifted, raised, moved, etc.) allows rotating flange 844 to rotate thereby causing rotation 872 in column 870. Release of pin 846 allows pin 846 to insert in one of the plurality of detents in rotating flange 844 which prevents further rotation of rotating flange 844 thereby preventing rotation of column 870. In some embodiments, the detents are positioned in 5°, 10°, 15°, or 20° increments relative to on another. In other embodiments, the detents may be positioned in 0 to 25° increments, 25 to 50° increments, 50 to 75° increments, 75 to 100° increments, 100 to 125° increments, 125 to 150° increments, 150 to 175° increments, 175 to 200° increments, 200 to 225° increments, 225 to 250° increments, 250 to 275° increments, 270 to 300° increments, 300 to 325° increments, 325 to 350° increments, or any range or subrange therebetween. Column 870 pivots or rotates (arrow 872) relative to the body 864 so that base 860 is positionable perpendicular to the patient or surface on which the base 860 rests and the column 870 is pivotable relative to the patient to position a clamp in proximity to a bodily opening or incision of a patient.

Figure 9:
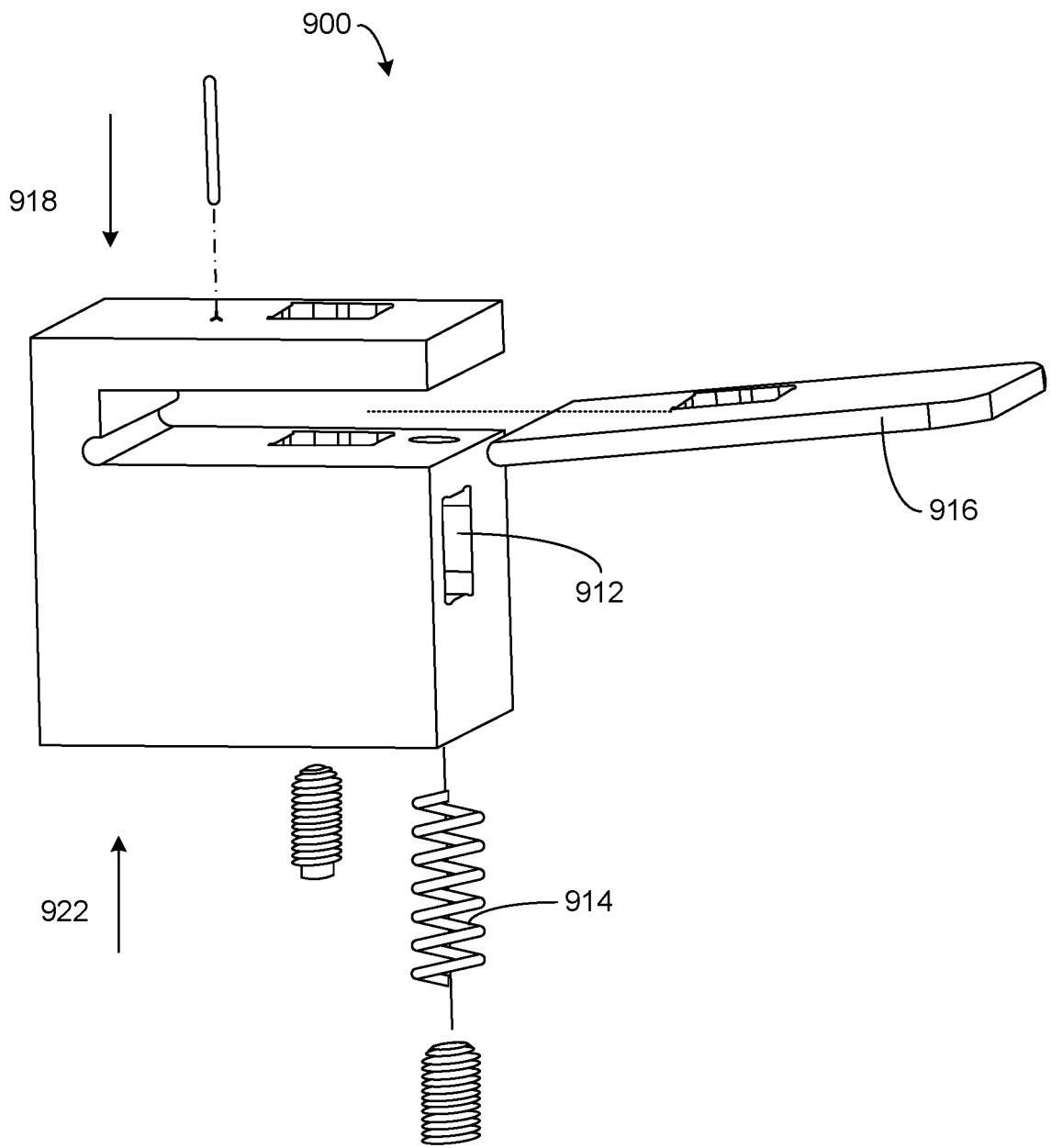
FIG. 9 illustrates an exploded view of one embodiment of an adjustable block of an endoscope control device.

Returning to FIG. 4, an endoscope control device 410 further includes an arm 480 extending horizontally, in an xz-plane, from the column 470. The arm 480 functions to enable positioning of a clamp 450 in proximity to a bodily opening or incision of a patient. Arm 480 is configured to translate vertically (arrow 484), along a y-axis, along the column 470 via adjustable block 900, as shown in FIG. 9. Adjustable block 900 defines arm receiving aperture 912 into which an arm, such as arm 480, is insertable and, in some embodiments, translatable therein. For example, arm 480 further comprises one or more detents 478 along its length so that arm 480 translates horizontally through adjustable block 900 (arrow 482), along an x-axis, relative to the column 470 and locks into position at any one of the detent locations within the adjustable block 900, as shown in FIGS. 4 and 9.

Further, as shown in FIGS. 4 and 9, movement 484 of arm 480 in a y-direction relative to column 470 is also through adjustable block 900. Adjustable block 900 further comprises a spring 914 loaded cam action plate 916. The plate 916 is spring 914 biased to maintain position of the adjustable block 900 when a downward force 918 is applied on adjustable block 900, arm 480, and/or clamp 450. In some embodiments, column 450 includes one or more serrations configured to maintain position of the adjustable block 900 when an upward force 922 is applied to adjustable block 900, arm 480, and/or clamp 450. In other embodiments, adjustable block 900 further includes a second cam action plate that is spring-biased and configured to maintain position of the adjustable block 900 when an upward force 922 is applied on adjustable block 900, arm 480, and/or clamp 450.

Figure 5A:
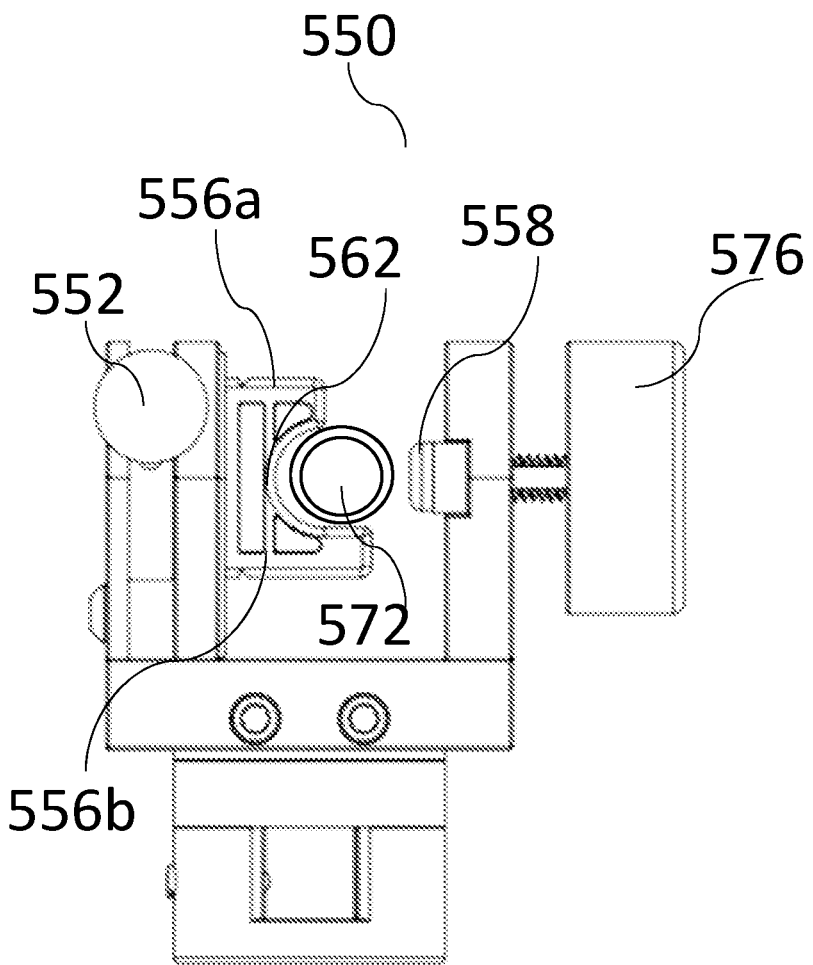
FIG. 5A illustrates a side view of one embodiment of a clamp of an endoscope control device, the clamp being in an open, unclamped configuration.
Figure 5B:
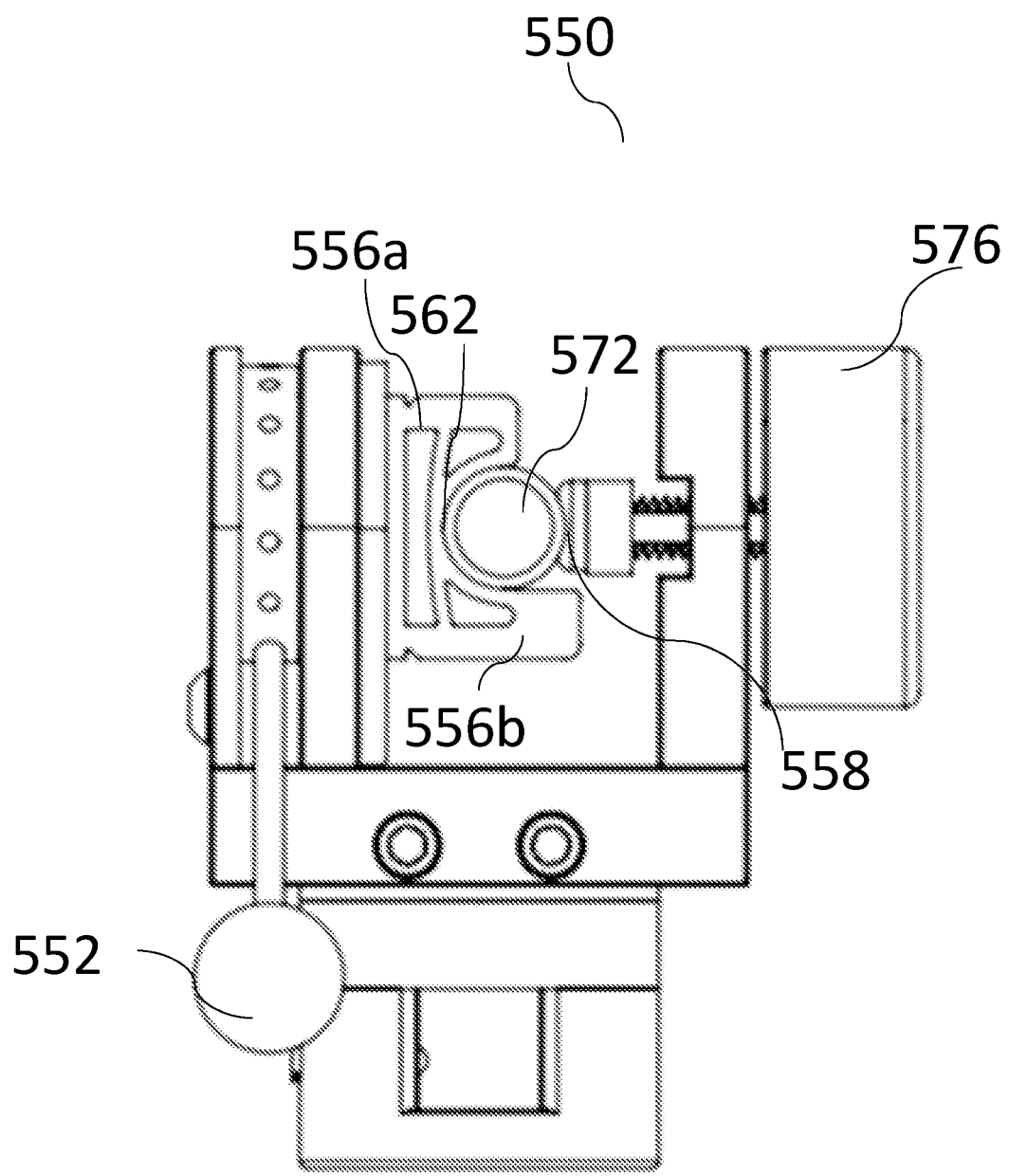
FIG. 5B illustrates a side view of the clamp of FIG. 5A in a closed, clamped configuration.
Figure 6:
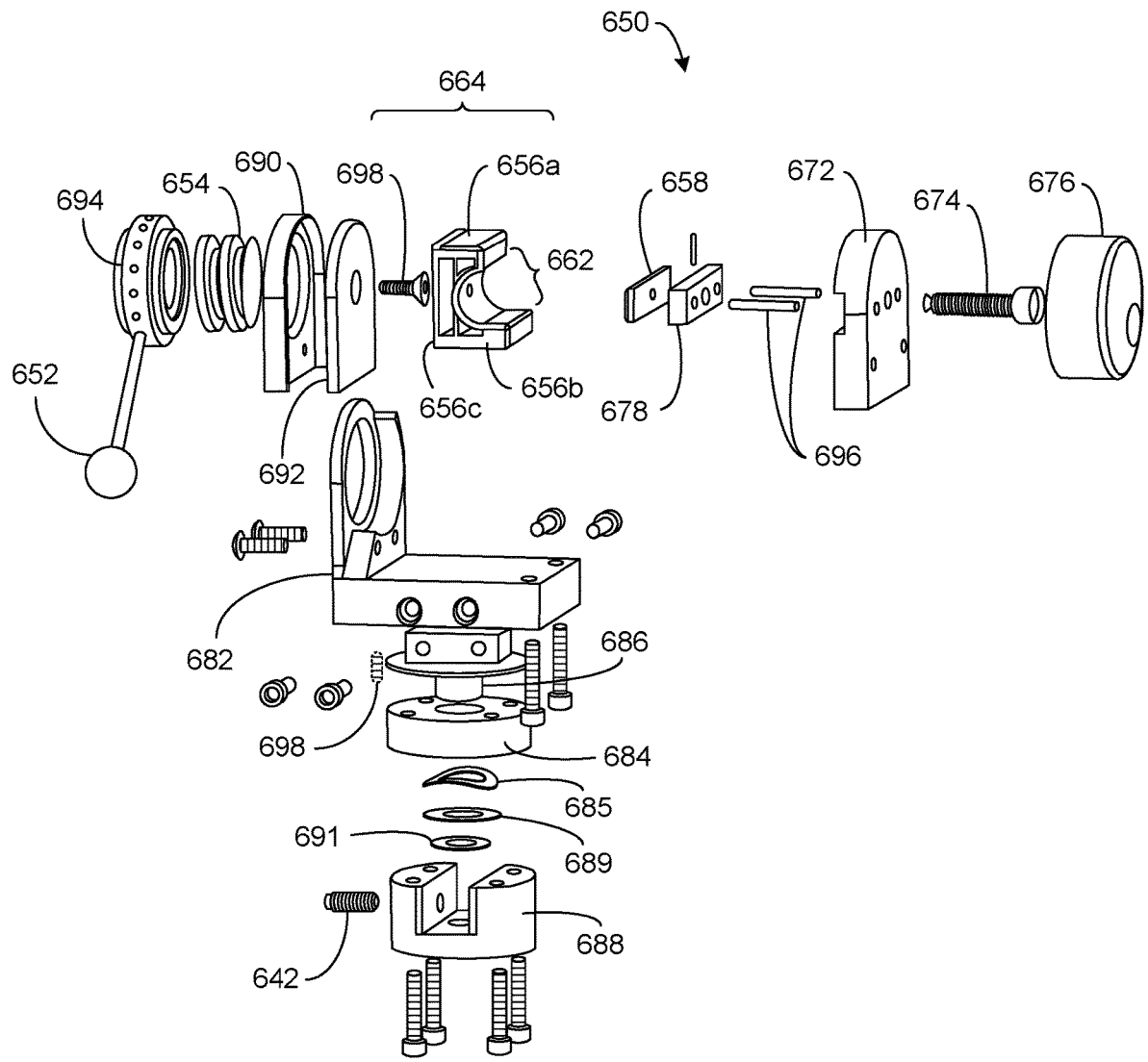
FIG. 6 illustrates an exploded view of the clamp of FIG. 5A.

Turning to FIGS. 5A-6, an endoscope control device further includes a clamp 550, 650. As shown in FIG. 5A, clamp 550 functions to receive endoscope 572 therein and apply a force circumferentially to the endoscope 572 to reduce or prevent axial and/or rotational translation of the endoscope 572 and to avoid discrete loading on the sides of the endoscope 572. Various clamp configurations are shown in FIGS. 5A-6 and 10-12. Focusing on an exploded view of clamp 650 shown in FIG. 6, clamp 650 is actuatable via lever 652 and lead screw 654 on a first side or holder side of the clamp and knob 676 and lead screw 674 on a second side or pad side of the clamp. Plate 690 defining aperture 697 interfaces with threads of lead screw 654, allowing wall 692 to be pushed and pulled with the lead screw 654. A holder 664 includes a first or top sidewall 656a and a second or bottom sidewall 656b, which together define an endoscope receiving area 662. Endoscope receiving area 662 defines a substantially hemi-cylindrical shaped surface for contacting and forcibly restraining an endoscope received therein. The first or top sidewall 556a, 656a and the second or bottom sidewall 556b, 656b are movable or transitionable between a first or open configuration (FIG. 5A) in which the first or top sidewall 556a, 656a and the second or bottom sidewall 556b, 656b are configured to set apart from an endoscope 572 when positioned in the endoscope receiving area 562, 662, as shown in FIGS. 5A-6, and a second or closed or clamped configuration (FIG. 5B) in which the first sidewall 556a, 656a and the second sidewall 556b, 656b are configured to clamp the endoscope 572 when positioned in the endoscope receiving area 562, 662, as shown in FIG. 5B. In some embodiments, holder 664 comprises an asymmetric holder such that the second sidewall 656b is longer than the first sidewall 656a. For example, a second sidewall 656b may be 10% to 15%, 15% to 20%, 20% to 25%, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90%, 90% to 95%, or 95% to 100% longer than a first sidewall 656a. In such asymmetric holder embodiments, the endoscope is configured to rest on the second sidewall 656b when the asymmetric holder is in the first or open or unclamped configuration. Alternatively or additionally, holder 664 further includes a third sidewall 656c that further forms or defines a hemicylindrical surface of endoscope receiving area 662.

Lever 652 is configured to move the first sidewall 656a and second sidewall 656b between the first and second configurations. For example, lever 652 may be movable between two configurations, for example a released or unclamped configuration as in FIG. 5A and an actuated or clamped configuration as in FIG. 5B, or a plurality of positions to effectuate movement of the first sidewall 656a and the second sidewall 656b. Further for example, in some embodiments, lever 652 effectuates movement of the first and second sidewalls 656a, 656b between one or more intermediate configurations between the first and second configurations. As lever 652 is used to rotate lever body 694, lead screw 654 is advanced, pushing wall 692 and holder 664 with endoscope 572 positioned therein against pad 658 and one or more supporting elements of pad 658 (e.g., plate 678, lead screw 674 that is mounted in support wall 672). This movement of lead screw and ultimately holder 664 is configured to cause an inward movement of sidewalls 656a, 656b, resulting in an area of the endoscope receiving area 662 to be reduced such that the sidewalls 656a, 656b increase a circumferential contact with an endoscope positioned in the endoscope receiving area 662. This circumferential contact about the endoscope 572 grips the endoscope 572 similar to that imposed by a human hand and fingers. Continued motion of lever 652 increases the advancement of holder 664 towards pad 658, resulting in increasing circumferential contact and therefore grip force about the endoscope body.

In some embodiments, as lever 652 is actuated 90 degrees, lead screw 654 is advanced ¼ inch; in other embodiments, lever 652 is actuated n degrees (e.g., n equals any number from 1-360 degrees) which advances the lead screw 0 to 1 inch, for example 0 to 0.1 inches, 0.1 to 0.2 inches, 0.1 to 0.25 inches, 0.2 to 0.3 inches, 0.3 to 0.4 inches, 0.4 to 0.5 inches, 0.5 to 0.6 inches, 0.6 to 0.75 inches, 0.7 to 0.8 inches, 0.8 to 0.9 inches, 0.9 to 1 inch, etc. One or more detents or grooves in lever body 694 interact with a spring-loaded ball detent mechanism 698 (which is fixed in support 682) to enable lever 652 to lock into any one of the positions. In some embodiments, an operator of the lever 652 or clamp 650 may receive audible (e.g., ball detent mechanism click), haptic (e.g., piezoelectric mechanism in lever body that initiates vibration when locked into any one of the positions, a user feeling a click of the detent mechanism, etc.), and/or visual (e.g., light is activated when locked into any one of the positions) feedback to indicate when the lever 652 is locked into any one of the positions.

Further, as shown in FIGS. 5A-6, an endoscope control device 550, 650 includes a pad 558, 658 opposite the endoscope receiving area 562, 662. Pad 558, 658 functions to contact an endoscope 572 positioned in clamp 550, 650 to prevent endoscope 572 from being displaced from endoscope receiving area 562, 662 as sidewalls 656a, 656b (optionally) 656c are moved from a first configuration to a second configuration to clamp the endoscope therein. Additionally, pad 558, 658 functions as a static wall that functions as a stop for advancement of holder 664. As such, pad 558, 658 is movable between a first or open position, as shown in FIG. 5A and a second or closed position, as shown in FIG. 5B. In the second or closed position, pad 558, 658 applies a force to endoscope 572 positioned therein. Pad 558, 658 may further include one or more or a plurality of intermediate configurations such that pad 558, 658 is adjustable to allow for endoscope of varying diameters. As shown in FIG. 6, knob 676 rotates lead screw 674 through support wall 672, which moves plate 678 coupled to pad 658 either forward to contact an endoscope positioned therein or retracts plate 678 coupled to pad 658 to disengage from an endoscope positioned therein. Plate 678 is prevented from rotating with lead screw 674 by dowel pins 696 which are fixed in plate 678, but slide freely in support wall 672, thereby supplying rotational resistance of plate 678.

Support 682 functions as a platform for coupling together various elements of clamp 650. Support 682 rotates relative to flange 684 on pivot 686 which is fixed to support 682. Base 688 is attached to flange 684 (via one or more fasteners, for example 4 screws), and is coupled to an arm of the endoscope control device. Washer 689, wave spring 685, and external ring clip 691 collectively function to secure flange 684 to pivot 686 and provide rotational friction. In some embodiments, base 488 translates horizontally (arrow 482) along arm 480, as shown in FIG. 4, via a complementary detent mechanism in arm 480 and base 488. For example, spring-loaded ball detent 642 (shown in FIG. 6) interacts with the one or more detents 478 along arm 480 (shown in FIG. 4). In other embodiments, base 488 is fixedly connected to arm 480 at a distal end 486 (or any position along arm 480) of arm 480.

Figure 10A:
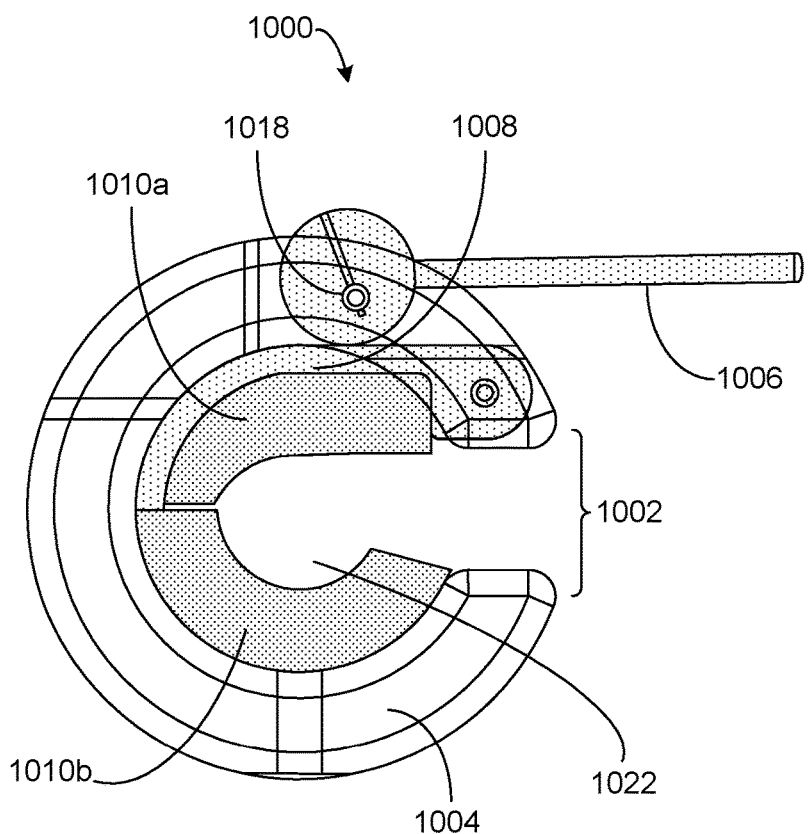
FIGS. 10A-10B illustrate another embodiment of a clamp of an endoscope control device in an open and a closed configuration, respectively.
Figure 10B:
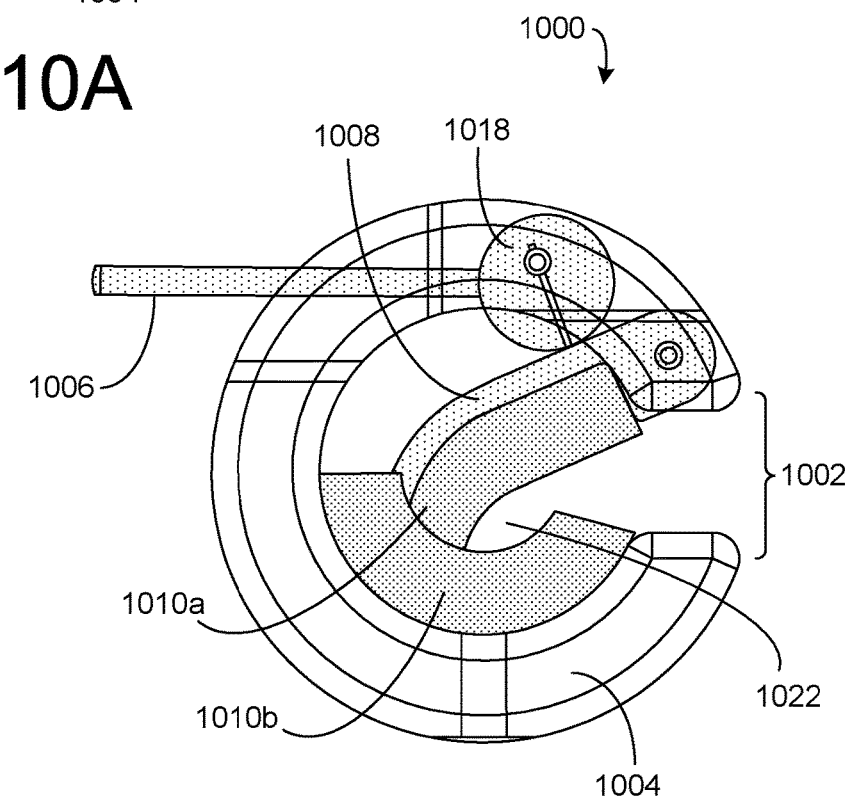

Turning now to FIGS. 10A-12B, which show alternative clamp embodiments. FIG. 10A shows clamp 1000 in the open, unloaded configuration, and FIG. 10B shows clamp 1000 in the closed, clamped configuration. Clamp 1000 shown in FIGS. 10A-10B comprises holder 1004 which defines entry aperture 1002 through which an endoscope is inserted into clamp 1000 and endoscope receiving area 1022 in which an endoscope is clamped by sidewall 1008 and pads 1010a, 1010b. FIG. 10B shows clamp 1000 in a closed or clamped configuration such that an endoscope positioned in endoscope receiving area 1022 is restrained axially and/or rotationally. In the closed configuration, eccentric lever 1006 (i.e., cam action lever) is configured to displace sidewall 1008 and pad 1010a to restrain an endoscope positioned in endoscope receiving area 1022. Sidewall 1008 and pad 1010a is preferably curved so that it contacts an endoscope positioned therein along a circumferential line of the endoscope. In an open or unclamped configuration, as shown in FIG. 10A, eccentric lever 1006 does not substantially displace sidewall 1008 and pad 1010a such that sidewall 1008 and pad 1010a is in proximity to a center of rotation 1018 of eccentric lever 1006 and an endoscope positioned within clamp 1000 is unrestrained.

Figure 11A:
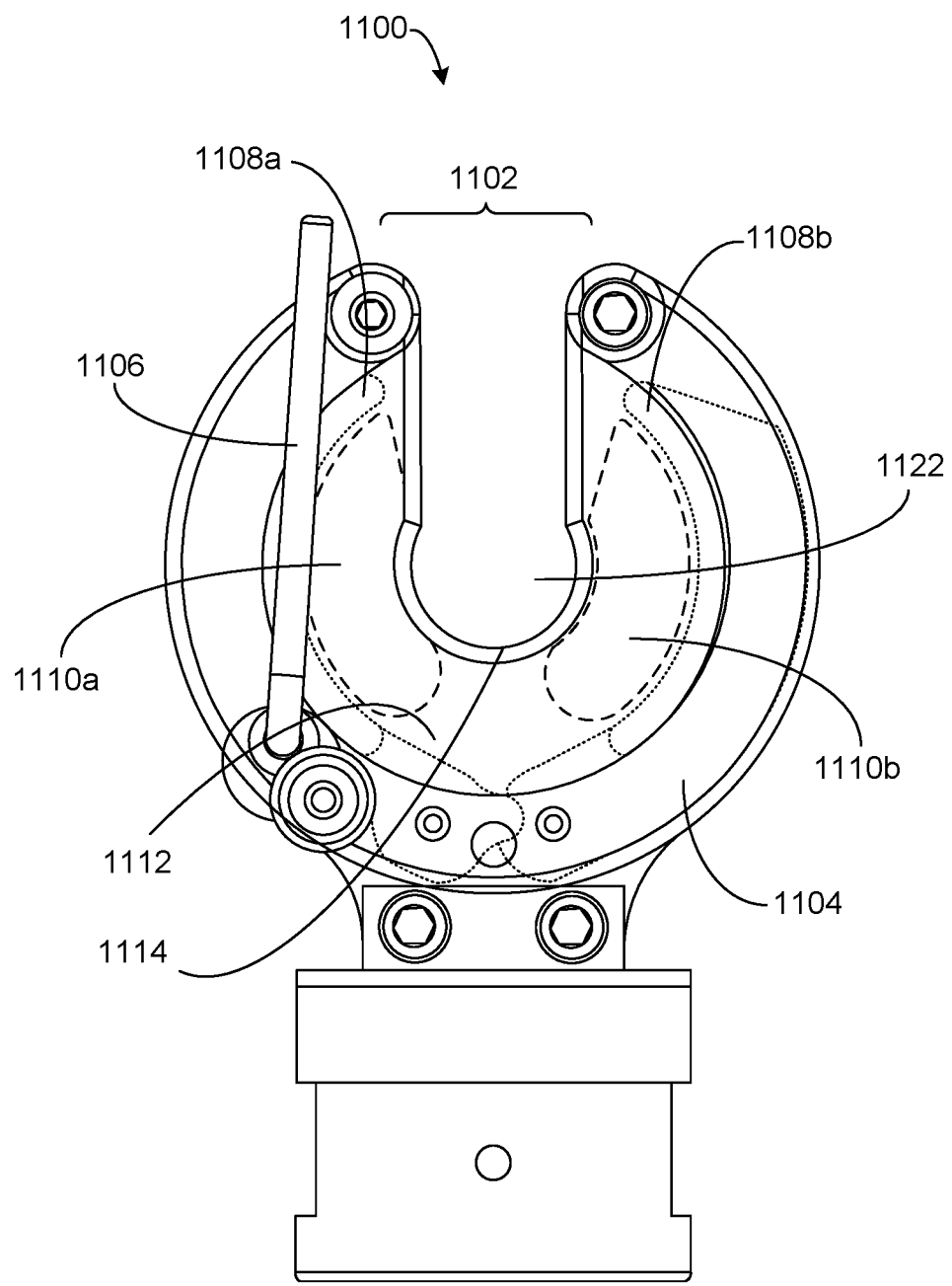
FIGS. 11A-11B illustrate another embodiment of a clamp of an endoscope control device in an open and a closed configuration, respectively.
Figure 11B:
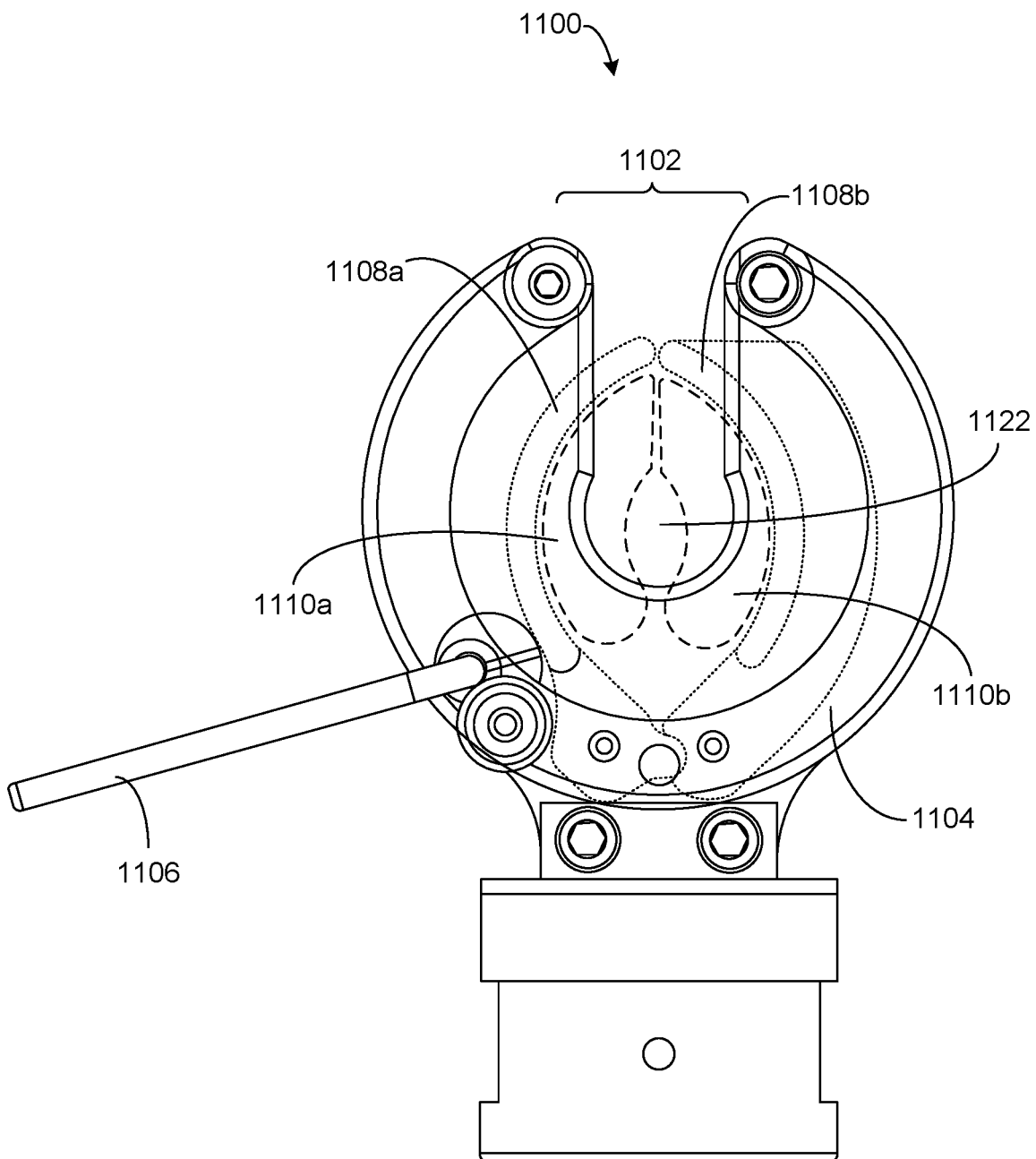

Turning to FIGS. 11A-11B which show an alternative embodiment of a clamp 1100. As shown in FIG. 11B, in a closed or clamped configuration, eccentric lever 1106 activates sidewalls 1108a, 1108b which cause pads 1110a, 1110b to contact an endoscope positioned within holder 1104 on opposing sides of the endoscope to axially and/or rotationally restrain the endoscope. Holder 1104 defines endoscope receiving area 1122 for holding an endoscope during clamping. The endoscope is positioned in holder 1104 through entry aperture 1102 defined by holder 1104. In an open or unclamped configuration, as shown in FIG. 11A, eccentric lever 1106 does not substantially displace sidewalls 1108a, 1108b and therefore pads 1110a, 1110b such that an endoscope positioned within clamp 1100 is unrestrained. Further, side plates 1112 (one on each side of holder 1104) guide the endoscope into the endoscope receiving area 1122. Inner edges 1114 of side plates 1112 maintain the endoscope elevated above a surface of the pads 1110a, 1110b when the endoscope is unlocked to allow the endoscope to move freely in holder 1104.

Figure 12A:
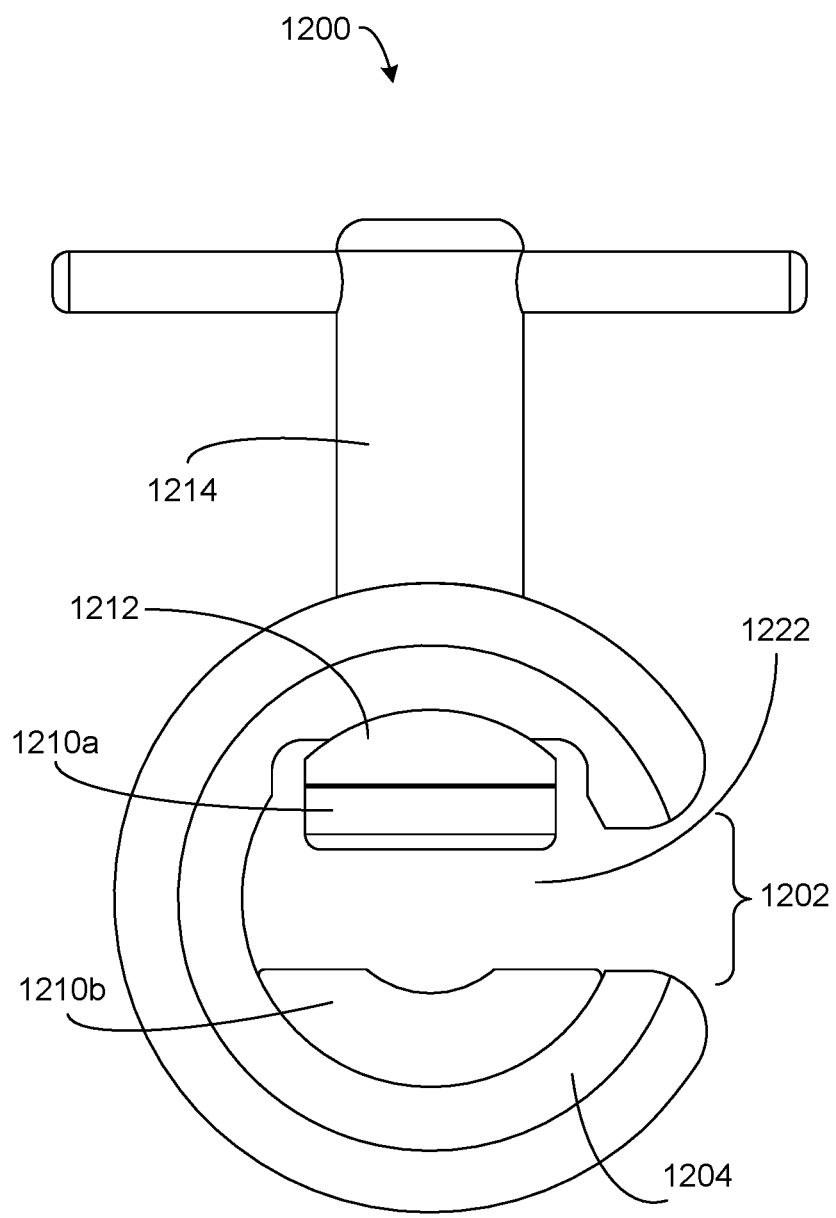
FIGS. 12A-12B illustrate another embodiment of a clamp of an endoscope control device in an open and a closed configuration, respectively.
Figure 12B:
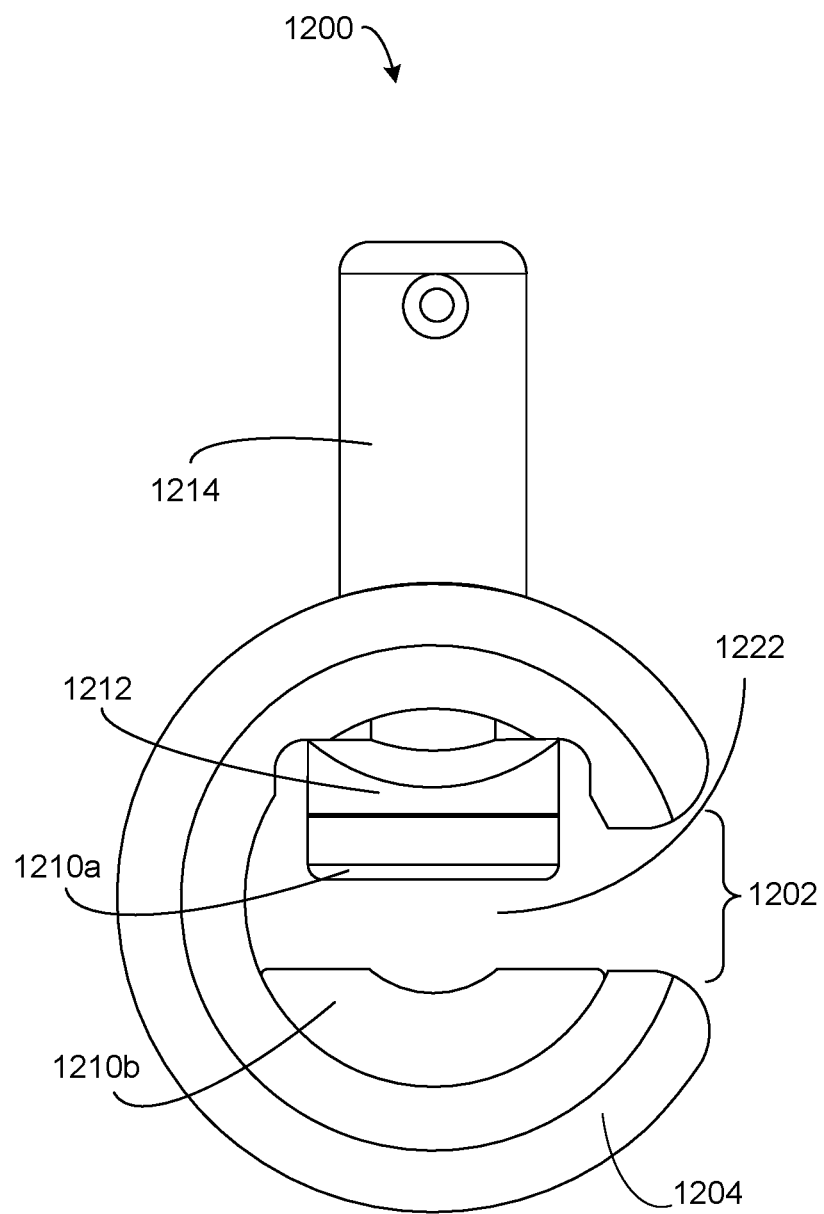

Turning to FIGS. 12A-12B which show another embodiment of a clamp 1200. As shown in FIG. 12B, holder 1204 defines entry aperture 1202 through which an endoscope is inserted into clamp 1200 and into endoscope receiving area 1222 which holds an endoscope during clamping. In a clamped or closed configuration, as shown in FIG. 12B, rotating rotatable column 1214 (e.g., 90 degrees, 45-90 degrees, 75 to 100 degrees, etc.) will rotate pusher 1212, causing it to displace downward due to its upper curved cam surface interacting with the inner curved surface of the holder 1204. This will cause pad 1210a to advance towards pad 1210b in holder 1204, thereby clamping an endoscope in between pads 1210a, 1210b. In an open or unclamped configuration, as shown in FIG. 12A, rotatable column 1214 is retracted via a compression spring that maintains the upper surface of pusher 1212 against the inner surface of holder 1204, so that it does not contact or restrain an endoscope positioned in endoscope receiving area 1222.

Figure 13:
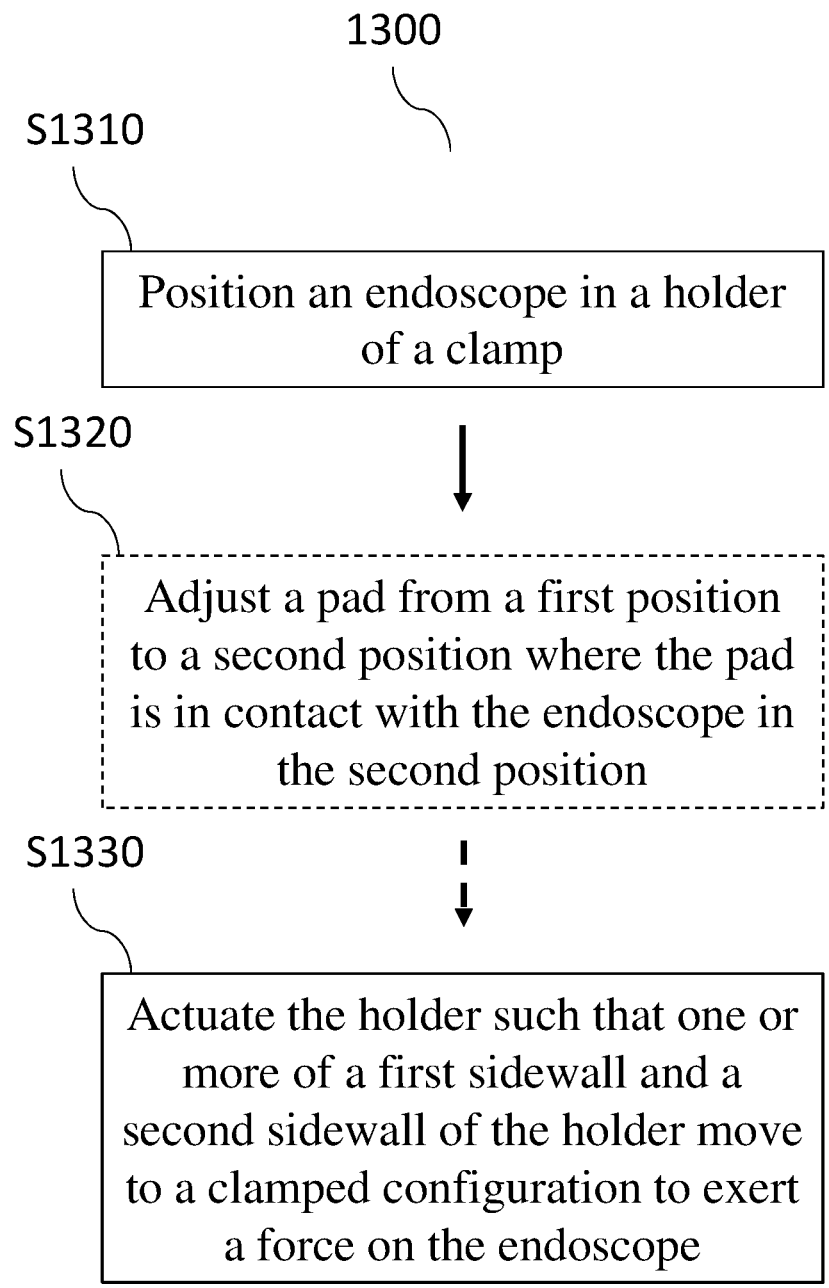
FIG. 13 illustrates a flow diagram of one embodiment of a method of using an endoscope control device.

Turning to FIG. 13, which shows a method 1300 of using one or more endoscope control devices described elsewhere herein. As shown in FIG. 13, a method of using one or more endoscope control devices includes positioning an endoscope in a holder of a clamp S1310; optionally (indicated by dashed lines around block S1320) adjusting a pad from a first position to a second position, wherein, in the second position, the endoscope is configured to contact a second surface of the endoscope that is opposite a first surface of the endoscope that is in contact with the holder S1320; and actuating the holder such that one or more of a first sidewall and/or a second sidewall of the holder move to a second or clamped configuration to exert a force to restrict axial and/or rotational movement of the endoscope S1330.

The method 1300 preferably functions with any of the clamps described elsewhere herein. In embodiments of FIG. 12, a sidewall is replaced with an end of a rotatable pin. In at least the embodiments of the clamp of FIGS. 5A-6, a circumferential force is applied to an outer diameter of an endoscope positioned therein by a first and second sidewall of the holder. In embodiments in which the holder is asymmetrical (FIGS. 5A-6) or substantially annular (FIGS. 10-12), the endoscope rests on a second sidewall of the holder or on an inner diameter of the annular ring of the holder when one or more of a first sidewall and a second sidewall are in a first, open or unclamped configuration.

One aspect of the present disclosure is directed to a device for reversibly constraining an endoscope. The device may include a base positionable proximate a patient. In any of the preceding embodiments, the surface may be a bed, a floor, a stand, a tripod, or the like. In any of the preceding embodiments, the device may further include a column extending vertically from the base. In any of the preceding embodiments, the column may be pivotally coupled to the base. In any of the preceding embodiments, the device may include an arm extending horizontally from the column. In any of the preceding embodiments, the arm may be configured to translate vertically along the column. In any of the preceding embodiments, the arm may be configured to translate horizontally relative to the column. In any of the preceding embodiments, the device may include a clamp coupled to the arm. In any of the preceding embodiments, the clamp may be configured to pivot relative to the arm. In any of the preceding embodiments, the clamp may include a holder comprising a first sidewall and a second sidewall.

In any of the preceding embodiments, the first sidewall and/or the second sidewall may be curved such that a radius of curvature may be anywhere from 2 mm to 15 mm or 0.1 inches to 0.5 inches. Alternatively, in any of the preceding embodiments, the first and second sidewall are planar such that the holder includes a third curved or U-shaped sidewall having a radius of curvature anywhere between and including 2 mm to 15 mm.

In any of the preceding embodiments, the first sidewall and the second sidewall together define an endoscope receiving area. Alternatively, in any of the preceding embodiments, the first, second, and third sidewall form an endoscope receiving area. Still alternatively, in any of the preceding embodiments, the holder comprises a monolithic component that deforms to grip an endoscope and returns to an undeformed state to release the endoscope.

In any of the preceding embodiments, the holder is transitionable between a first configuration in which the first sidewall and the second sidewall are configured to clamp an endoscope when positioned in the endoscope receiving area and a second configuration in which the first sidewall and the second sidewall are configured to set apart from the endoscope when positioned in the endoscope receiving area. Alternatively, in any of the preceding embodiments, the holder is transitionable between a first configuration in which the first, second, and third sidewall are configured to clamp an endoscope when positioned in the endoscope receiving area and a second configuration in which the first, second, and third sidewall are configured to set apart from the endoscope when positioned in the endoscope receiving area.

In any of the preceding embodiments, the device may include a pad opposite the endoscope receiving area. In any of the preceding embodiments, the pad is movable between a first position in which the pad contacts the endoscope when positioned in the endoscope receiving area and a second position in which the pad does not contact the endoscope when positioned in the endoscope receiving area.

In any of the preceding embodiments, when the holder is in the first configuration and the pad is in the second position, the endoscope is prevented from translational movement.

In any of the preceding embodiments, when the holder is in the first configuration and the pad is in the second position, the endoscope is prevented from rotational movement.

In any of the preceding embodiments, when the holder is in the first configuration and the pad is in the second position, the endoscope is prevented from translational and rotational movement.

In any of the preceding embodiments, the holder comprises an asymmetric holder such that the second sidewall is longer than the first sidewall.

In any of the preceding embodiments, the holder comprises an asymmetric holder such that a first side of a monolithic holder is longer than a second side of a monolithic holder.

In any of the preceding embodiments, the endoscope is configured to rest on the second sidewall or the second side when the asymmetric holder is in the second configuration.

In any of the preceding embodiments, the pad is configured to apply a force to the endoscope when in the first position.

In any of the preceding embodiments, the first and second sidewalls are configured to apply a force to the endoscope when in the first configuration. Alternatively, in any of the preceding embodiments, the first, second, and third sidewalls are configured to apply a force to the endoscope when in the first configuration. Alternatively still, in any of the preceding embodiments, the first and second side of a monolithic holder are configured to apply a force to the endoscope when in the deformed configuration.

In any of the preceding embodiments, the column is configured to pivot relative to the base in 10° increments. Alternatively, in any of the preceding embodiments, the column is configured to pivot relative to the base in discrete increments. Alternatively still, in any of the preceding embodiments, the column is configured to infinitely pivot relative to the base. In any of the preceding embodiments, the column is configured to pivot relative to the base through a 180° range of motion. In any of the preceding embodiments, the column is configured to pivot relative to the base through 360° range of motion.

In any of the preceding embodiments, the clamp further comprises a lever configured to move the first and second sidewalls between the first and second configurations. Alternatively, in any of the preceding embodiments, the clamp further comprises a lever configured to move the first, second, and third sidewalls between the first and second configurations. Alternatively still, in any of the preceding embodiments, the clamp further comprises a lever configured to move the first and second sides of a monolithic clamp between the deformed and undeformed configurations.

In any of the preceding embodiments, the first and second sidewalls are further configured to move between one or more intermediate configurations between the first and second configurations. Alternatively, in any of the preceding embodiments, the first, second, and third sidewalls are configured to move between one or more intermediate configurations between the first and second configurations. Alternatively still, in any of the preceding embodiments, the first and second side of a monolithic holder are configured to move between one or more intermediate configurations between the deformed and undeformed configurations.

In any of the preceding embodiments, the lever is movable between a plurality of positions to move the first and second sidewalls between the one or more intermediate configurations and the first and second configurations. Alternatively, in any of the preceding embodiments, the lever is movable between a plurality of positions to move the first, second, and third sidewalls between the one or more intermediate configurations and the first and second configurations. Still alternatively, in any of the preceding embodiments, the lever is movable between a plurality of positions to move the first and second sides of the monolithic holder between the one or more intermediate configurations and the deformed and undeformed configurations.

In any of the preceding embodiments, all or a part of the clamp is disposable.

In any of the preceding embodiments, the clamp is further configured to translate horizontally along the arm.

In any of the preceding embodiments, the device further includes a clamp release mechanism. In any of the preceding embodiments, the clamp release mechanism may comprise a button, lever, pedal, etc. In any of the preceding embodiments, the clamp release mechanism may be manually actuated, pneumatically actuated, electrically actuated, hydraulically actuated, pressure activated, voice activated, gaze activated, automatically (e.g., using artificial intelligence or machine learning algorithms, etc.) etc.

In any of the preceding embodiments, the device further includes a surgical drape configured to cover at least the clamp.

Another aspect of the present disclosure is directed to a method of reversibly restraining an endoscope. In some embodiments, the method includes positioning an endoscope in a holder of a clamp; and actuating the holder such that one or more of a first sidewall and a second sidewall of the holder move to a clamped configuration to exert a force on the endoscope.

In any of the preceding embodiments, the method further includes adjusting a pad of the clamp from a first position to a second position where the pad is in contact with the endoscope in the second position.

In any of the preceding embodiments, the method further includes providing the clamp comprising the holder. In any of the preceding embodiments, the holder includes a the first sidewall and the second sidewall, such that the first sidewall and the second sidewall together define an endoscope receiving area, and such that the holder is transitionable between a first configuration in which the first sidewall and the second sidewall are configured to set apart from the endoscope when positioned in the endoscope receiving area and a second configuration in which the first sidewall and the second sidewall are configured to clamp the endoscope when positioned in the endoscope receiving area.

In any of the preceding embodiments, the method further includes coupling the clamp to an arm extending horizontally from a column, which extends vertically from a base.

In any of the preceding embodiments, the method further includes positioning the base proximate to a patient.

In any of the preceding embodiments, the method further includes positioning a surgical drape over the clamp.

In any of the preceding embodiments, the method further includes applying a force to an outer diameter of the endoscope positioned therein by the first and the second sidewall of the holder.

Another aspect of the present disclosure is directed to a device for reversibly constraining an endoscope. In some embodiments, the device includes a base positionable proximate a patient; a column extending vertically from the base; an arm extending horizontally from the column; and a clamp coupled to the arm.

In any of the preceding embodiments, the clamp includes a holder comprising an annular ring which defines an endoscope receiving area, such that the holder is transitionable between a first configuration in which the annular ring is set apart from an endoscope when positioned in the endoscope receiving area and a second configuration in which the annular ring is configured to clamp the endoscope when positioned in the endoscope receiving area.

In any of the preceding embodiments, the clamp further includes a pad opposite the endoscope receiving area, such that the pad is movable between a first position in which the pad does not contact the endoscope when positioned in the endoscope receiving area and a second position in which the pad contacts the endoscope when positioned in the endoscope receiving area.

In any of the preceding embodiments, the arm is configured to translate vertically along the column and horizontally relative to the column.

In any of the preceding embodiments, the clamp is configured to pivot relative to the arm.

In any of the preceding embodiments, when the holder is in the second configuration and the pad is in the second position, the endoscope is prevented from translational and rotational movement In any of the preceding embodiments, the holder comprises an asymmetric holder such that a second sidewall of the annular ring is longer than a first sidewall of the annular ring.

In any of the preceding embodiments, the endoscope is configured to rest on the second sidewall when the asymmetric holder is in the first configuration.

In any of the preceding embodiments, the pad is configured to apply a force to the endoscope when in the second position.

In any of the preceding embodiments, the annular ring is configured to apply a force to the endoscope when in the second configuration.

In any of the preceding embodiments, the column is pivotally coupled to the base.

In any of the preceding embodiments, the column is configured to pivot relative to the base in 10° increments.

In any of the preceding embodiments, the clamp further comprises a lever configured to move the first and second sidewalls between the first and second configurations.

In any of the preceding embodiments, all or a part of the clamp is disposable. In any of the preceding embodiments, the clamp is further configured to translate horizontally along the arm.

Another aspect of the present disclosure is directed to a device for reversibly constraining an endoscope. In some embodiments, the device includes a base positionable proximate a patient; a column extending vertically from the base; an arm extending horizontally from the column; and a clamp coupled to the arm. In some embodiments, the clamp includes: a holder comprising a first sidewall and a second sidewall, such that the first sidewall and the second sidewall together define an endoscope receiving area, and such that the holder is transitionable between a first configuration in which the first sidewall and the second sidewall are configured to set apart from an endoscope when positioned in the endoscope receiving area and a second configuration in which the first sidewall and the second sidewall are configured to clamp the endoscope when positioned in the endoscope receiving area.

In any of the preceding embodiments, the clamp further includes a pad opposite the endoscope receiving area, wherein the pad is movable between a first position in which the pad does not contact the endoscope when positioned in the endoscope receiving area and a second position in which the pad contacts the endoscope when positioned in the endoscope receiving area.

In any of the preceding embodiments, the arm is configured to translate vertically along the column and horizontally relative to the column.

In any of the preceding embodiments, the clamp is configured to pivot relative to the arm.

In any of the preceding embodiments, when the holder is in the second configuration and the pad is in the second position, the endoscope is prevented from translational and rotational movement In any of the preceding embodiments, the holder comprises an asymmetric holder such that the second sidewall is longer than the first sidewall.

In any of the preceding embodiments, the endoscope is configured to rest on the second sidewall when the asymmetric holder is in the first configuration.

In any of the preceding embodiments, the pad is configured to apply a force to the endoscope when in the second position.

In any of the preceding embodiments, the first and second sidewalls are configured to apply a force to the endoscope when in the second configuration.

In any of the preceding embodiments, the column is pivotally coupled to the base.

In any of the preceding embodiments, the column is configured to pivot relative to the base in 10° increments.

In any of the preceding embodiments, the clamp further comprises a lever configured to move the first and second sidewalls between the first and second configurations.

In any of the preceding embodiments, all or a part of the clamp is disposable.

In any of the preceding embodiments, the clamp is further configured to translate horizontally along the arm.

Although various movement mechanisms are herein contemplated, such as detent mechanisms, rotatable flanges, spring loaded balls or plates, etc., it is within one of skill in the art to modify such movement mechanisms and such modifications are also within the scope of this disclosure.

As used in the description and claims, the singular form "a", "an" and "the" include both singular and plural references unless the context clearly dictates otherwise. For example, the term "position" may include, and is contemplated to include, a plurality of positions. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of reversibly restraining an endoscope, comprising:
    positioning an endoscope in a holder of a clamp;
    actuating one or more sidewalls of the holder to at least a first clamped configuration such the endoscope remains axially and rotationally translatable;
    actuating the one or more sidewalls of the holder to at least a second clamped configuration such the endoscope is either axially or rotationally translatable;
    actuating the one or more sidewalls of the holder to at least a third clamped configuration such that the endoscope is neither axially nor rotationally translatable, wherein:
    the clamp comprises a respective detent or groove for the first clamped configuration, the second clamped configuration, and the third clamped configuration, and
    a ball detent mechanism configured to provide feedback to indicate the clamp is in the first clamped configuration, the second clamped configuration, or the third clamped configuration.

2. The method of claim 1, further comprising:
    transitioning the holder between the first clamped configuration in which a first sidewall of the one or more sidewalls is configured to set apart from the endoscope and the third clamped configuration in which the first sidewall and a second sidewall of the one or more sidewalls are configured to clamp the endoscope; and
    resting the endoscope on the second sidewall in the first clamped configuration.

3. The method of claim 2, further comprising coupling the clamp to an arm extending horizontally from a column, which extends vertically from a base.

4. The method of claim 2, wherein actuating the holder comprises actuating the holder to a plurality of configurations between the first clamped configuration and the third clamped configuration, wherein a force exerted by the holder is adjustable to restrict one or both of: an axial movement or a rotational movement of the endoscope.

5. The method of claim 4, further comprising positioning the clamp in proximity to a bodily opening or incision of a patient.

6. The method of claim 1, further comprising positioning a surgical drape over the clamp.

7. The method of claim 1, further comprising applying a circumferential force to an outer diameter of the endoscope positioned therein by a first sidewall of the one or more sidewalls of the holder and a second sidewall of the one or more sidewalls of the holder.

* * * * *